United States Patent
Chaiken et al.

(10) Patent No.: US 6,292,686 B1
(45) Date of Patent: Sep. 18, 2001

(54) APPARATUS AND METHOD FOR THERMAL TISSUE MODULATION

(75) Inventors: Joseph Chaiken, Fayetteville, NY (US); Charles M. Peterson, Potomac, MD (US)

(73) Assignee: LighTouch Medical, Inc., Bryn Athyn, PA (US)

( * ) Notice: Subject to any disclaimer, the term of this patent is extended or adjusted under 35 U.S.C. 154(b) by 0 days.

(21) Appl. No.: 09/295,975

(22) Filed: Apr. 21, 1999

Related U.S. Application Data

(60) Provisional application No. 60/083,039, filed on Apr. 24, 1998.

(51) Int. Cl.[7] ............................................. A61B 6/00
(52) U.S. Cl. ..................... 600/476; 600/473; 600/310; 600/121
(58) Field of Search ..................... 600/310, 473, 600/474, 475, 407, 549, 121, 316; 356/39, 301–303; 607/96, 99, 100, 102

(56) References Cited

U.S. PATENT DOCUMENTS

| | | |
|---|---|---|
| 5,159,929 | 11/1992 | Morris et al. . |
| 5,372,135 | 12/1994 | Mendelson et al. . |
| 5,800,350 * | 9/1998 | Coppleson et al. ................ 600/372 |
| 5,830,146 * | 11/1998 | Skladnev et al. . |
| 5,902,246 * | 5/1999 | McHenry et al. ................. 600/476 |

FOREIGN PATENT DOCUMENTS

| | | |
|---|---|---|
| 0 247 777 | 12/1987 | (EP) . |
| WO 92/22793 | 12/1992 | (WO) . |
| WO 93/00856 | 1/1993 | (WO) . |
| WO 96/03074 | 2/1996 | (WO) . |
| WO 96/29925 | 10/1996 | (WO) . |
| WO 97/36540 | 10/1997 | (WO) . |
| WO 98/03847 | 1/1998 | (WO) . |

\* cited by examiner

*Primary Examiner*—Marvin M. Lateef
*Assistant Examiner*—Shawna J Shaw
(74) *Attorney, Agent, or Firm*—Gates & Cooper LLP

(57) ABSTRACT

Disclosed is a tissue modulation device for use dining spectroscopy of tissue of a subject. In one embodiment, the device comprises an inner sheath, an outer sheath and a window disposed through the inner and outer sheaths, wherein the inner and outer sheaths comprise a sufficiently flexible material that the device can be secured to a region of tissue to be spectroscopically probed, wherein the inner and outer sheaths are joined to one another so that at least one temperature regulating element can be disposed between the inner and outer sheaths, and wherein the window is sufficiently transparent that electromagnetic radiation can be delivered to and collected from an underlying tissue through the inner and outer sheaths. The invention additionally provides a method of modulating temperature of tissue in a subject to be spectroscopically probed. In a preferred embodiment, the method comprises applying a tissue modulation device of the invention to the tissue, passing current through the temperature regulating element so as to elevate or lower the temperature of the tissue, and passing electromagnetic radiation through the window of the device. Preferably, spectroscopic probing is performed when the temperature of the tissue has been elevated or lowered and when the temperature of the tissue is not elevated or lowered. The method can further comprise collecting Raman spectra emitted by the tissue. The invention also provides a method for determining phase transition, and a method for determining lipid content and identity and protein content in a tissue of a subject.

26 Claims, 9 Drawing Sheets

APPARATUS AND METHOD FOR THERMAL TISSUE MODULATION

This application claims the benefit of U.S. provisional patent application Ser. No. 60/083,039, filed on Apr. 24, 1998, the entire contents of which are hereby incorporated by reference into this application. Throughout this application various publications are referenced. The disclosures of these publications in their entireties are hereby incorporated by reference into this application in order to more fully describe the state of the art to which this invention pertains.

TECHNICAL FIELD OF INVENTION

The invention relates to an apparatus and method for modulating temperature to alter tissue properties as well as blood and fluid content and flow in a tissue of a subject. The method facilitates the noninvasive measurement of analytes by modulating the temperature of the tissue being analyzed.

BACKGROUND OF THE INVENTION

There has long been considerable interest in the non-invasive monitoring of body chemistry. There are 16 million Americans with diabetes, all of whom would benefit from a method for non-invasive measurement of blood glucose levels. Using currently accepted methods for measuring blood glucose levels, many diabetics must give blood five to seven times per day to adequately monitor their health status. With a non-invasive blood glucose measurement, closer control could be imposed and the continuing damage, impairment and costs caused by diabetes could be minimized.

Blood oximetry is an example of an application of electronic absorption spectroscopy to non-invasive monitoring of the equilibrium between oxygenated and deoxygenated blood (U.S. Pat. No. 5,615,673, issued Apr. 1, 1997). Similarly, vibrational spectroscopy is a reliable mode of quantitative and qualitative ex vivo analysis for complex mixtures, and there are reports of in vitro applications of this method to metabolically interesting analytes (S. Y. Wang et al, 1993, Analysis of metabolites in aqueous solution by using laser Raman spectroscopy, Applied Optics 32(6):925–929; A. J. Berger et aL, 1996, Rapid, noninvasive concentration measurements of aqueous biological analytes by near infrared Raman spectroscopy, Applied Optics 35(1):209–212). Infrared measures, such as vibrational absorption spectroscopy, have been applied to skin tissue, but with success limited by unavailability of suitable light sources and detectors at crucial wavelengths, interference from water, and by heating of the tissue due to the absorption of incident radiation (U.S. Pat. No. 5,551,422, see also R. R. Anderson and J. A. Parrish, 1981, The Optics of Human Skin, J. Investigative Dermatology 77(1):13–19; K. Robinsen, 1998, Biophotonics Internatl 5(3):48–52). Previous attempts to provide methods for non-Invasive blood glucose monitoring are sunned in U.S. Pat. No. 5,553,616, issued on Sep. 10, 1996.

Optimal application of noninvasive techniques for blood analysis will require improved methods for isolating signals attributable to blood versus surrounding tissues.

SUMMARY OF THE INVENTION

To overcome the limitations of the prior art, the invention provides a device and method for thermal tissue modulation. The device and method can be used with noninvasive spectroscopy, such as Raman spectroscopy, for the analysis of various features of tissue and blood in a subject.

The invention provides a tissue modulation device for use during spectroscopy of tissue of a subject. In one embodiment, the device comprises an inner sheath, an outer sheath and a window disposed through the inner and outer sheaths, wherein the inner and outer sheaths comprise a sufficiently flexible material that the device can be secured to a region of tissue to be spectroscopicaly probed, wherein the inner and outer sheaths are joined to one another so that at least one temperature regulating element can be disposed between the inner and outer sheaths, and wherein the window is sufficiently transparent that electromagnetic radiation can be delivered to and collected from an underlying tissue through the inner and outer sheaths.

In another embodiment, the device comprises means for altering the temperature of a region of tissue in a subject; means for securing the device to the tissue; and a window, wherein the window is sufficiently transparent that electromagnetic radiation can be delivered to and collected from an underlying tissue through the device. In one embodiment, the means for securing the device to tissue comprises a sheath, a fingerstall, a cuff, a strap, a molded sample holder or an adhesive.

In a preferred embodiment, the device further comprises a temperature regulating element disposed between the inner and outer sheaths. The device can further comprise a temperature sensing element disposed between the inner and outer sheaths. Preferably, the temperature regulating element comprises wire, such as, for example, teflon-coated nichrome. The temperature regulating element can include a heating element, or a cooling element, or both a heating and cooling element. Preferably, the device further comprises a heat transfer fluid within the space between the inner and outer sheaths. Examples of heat transfer fluid include, but are not limited to, glycerol, silicone and oil, such as olive oil. The heat transfer fluid can comprise a deuterated molecule.

In one embodiment of the device, the window comprises a substantially annular opening in the inner and outer sheaths. In another embodiment, the window comprises a lens. The window is preferably about 1 mm to about 10 mm in diameter.

The inner and outer sheaths of the device can be substantially cylindrical in shape, comprise a fingerstall, and/or comprise a cuff. Preferably, the flexible material comprises latex.

The invention additionally provides a method of modulating temperature of tissue in a subject to be spectroscopically probed. In a preferred embodiment, the method comprises applying a tissue modulation device of the invention to the tissue, passing current through the temperature regulating element so as to elevate or lower the temperature of the tissue, and passing electromagnetic radiation through the window of the device. Preferably, spectroscopic probing is performed when the temperature of the tissue has been elevated or lowered and when the temperature of the tissue is not elevated or lowered. The method can further comprise collecting Raman spectra emitted by the tissue.

The invention also provides a method for monitoring phase transitions, and thereby a method for determining lipid content and identity and protein content in a tissue of a subject. In a preferred embodiment, the method comprises applying a tissue modulation device of the invention to the tissue, passing current through the temperature regulating element so as to elevate or lower the temperature of the tissue, and passing electromagnetic radiation through the window of the device. Preferably, spectroscopic probing is performed when the temperature of the tissue has been elevated or lowered and when the temperature of the tissue is not elevated or lowered. The method can further comprise collecting Raman spectra emitted by the tissue. The collected spectra are then analyzed to determine the lipid content, lipid identity and/or protein content and identity of the tissue. Preferably, the analysis comprises determining the difference in number of Raman shifted photons emitted by the tissue at different temperatures.

DETAILED DESCRIPTION

Figure 1:
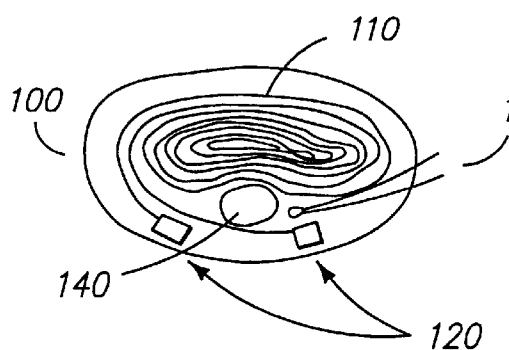
FIG. 1 is a front view of a tissue modulation device adapted to fit a fingertip.

The invention disclosed herein describes an apparatus for the manipulation of temperature in tissue modulation. The apparatus can be used noninvasively. The apparatus provides control of the tissue temperature during modulation. The apparatus modulates tissue properties as well as blood flow and content using either thermally induced vasodilatation and vasoconstriction, or thermally induced lipid-based order is order transitions or protein unfolding dynamics. When tissue temperature is lowered, blood flow to and from the region of tissue is diminished When tissue temperature is raised, blood flow returns to the affected tissue. Manipulation of flow and temperature allows more complete modulation of blood and fluid content. The difference between measurements taken in the blood replete and blood depleted states provides a measure indicative of components in the blood while muirnizuig the effects of extraneous spectroscopic signals due to callouses, oils, dirt, soap residue and other sources associated with the surrounding tissue. When thermal tissue modulation is employed during noninvasive spectroscopy, for example, the analysis can include determining the difference between the spectra collected in the blood replete and the blood depleted states. The method can also involve inducing changes in protein folding and lipid states of aggregation. These changes can be used to determine lipid identity and content or protein identity and content in blood and surrounding tissues. The methods can also be used to determine analyte concentrations, such as glucose, urea, triglycerides, creatine, lactate, pyruvate, and others.

Definitions

All scientific and technical terms used in this application have meanings commonly used in the art unless otherwise specified. As used in this application, the following words or phrases have the meanings specified.

As used herein, "tissue" means any portion of an organ or system of the body, including, but not limited to, skin, capillary beds, blood, muscle, breast and brain. Preferably, the tissue is blood in capillary beds of a fingertip.

As used herein, "blood replete" refers to a state in which blood flow through and interstitial fluid content of a tissue is unobstructed by, for example, vasoconstriction induced by cooling or the application of pressure. The blood replete state can be enhanced by conditions which increase vasodilatation, such as warning.

As used herein, "blood depleted" refers to a state in which blood flow through and interstitial fluid content of a tissue is substantially restricted and blood volume is mined. A blood depleted state can be achieved by, for example, cooling and/or applying pressure to the issue.

As used herein, "sheath" refers to a material capable of being applied to a region of tissue to be spectroscopically probed. A sheath can circumscribe a region of tissue, such as a fingertip or ear lobe. Alternatively, the sheath can conform to a surface of tissue, and be held in place with straps, adhesive or other material.

As used herein, "flexible" refers to the property of a sheathing material allowing it to adopt various conformations.

As used herein, "secured" to a region of tissue means that the device will be capable of maintaining steady and continuous contact with the tissue for a period of minutes such that reasonably reliable measurements can be taken from the tissue. The device may be applied to the tissue, as a fingerstall fitted to a fingertip. Alternatively, the tissue may be applied to the device, as a fingertip placed in a molded sample holder or strapped to a solid surface.

As used herein, "heat transfer fluid" is a thermally stable, electrically insulating fluid that facilitates distribution of heat or cold.

As used herein, "window" means an opening (absence of material) or a transparent material. The material is sufficiently transparent if electromagnetic radiation can be passed from a first side of the window, through the material to tissue of a subject positioned on the second side of the window, and light scattered by the tissue can be detected at or near the first side of the window.

As used herein, "Phase transition" or "order-disorder transition" refers to relative orientation and rigidity of arrangement of lipid side chains in interstitial fluids, capillary walls, membranes, blood, liposomes, etc.

As used herein, "a" means at least one, and can include a plurality.

Tissue Modulation Device

The invention disclosed herein provides a device that can be used for modulating temperature in a tissue. The device is suitable for use in conjunction with methods for measuring an analyte in the tissue. The device can be used noninvasively. The device is suitable for use during spectroscopy of tissue of a subject. In one embodiment, the device comprises an inner sheath, an outer sheath and a window disposed through the inner and outer sheaths, wherein the inner and outer sheaths comprise a sufficiently flexible material that the device can be secured to a region of tissue to be spectroscopically probed, wherein the inner and outer sheaths are joined to one another so that at least one temperature regulating element can be disposed between the inner and outer sheaths, and wherein the window is sufficiently transparent that electromagnetic radiation can be delivered to and collected from an underlying tissue through the inner and outer sheaths.

In a preferred embodiment, the device further comprises a temperature regulating element disposed between the inner and outer sheaths. The device can further comprise a temperature sensing element disposed between the inner and outer sheaths. Preferably, the temperature regulating element comprises wire, such as, for example, teflon-coated nichrome. The temperature regulating element can include a heating element, or a cooling element, or both a heating and cooling element provided in parallel. When both a heating element and a cooling element are employed, they can be under separate or coordinated control.

Preferably, the device further comprises a heat transfer fluid within the space between the inner and outer sheaths. Examples of heat transfer fluid include, but are not limited to, glycerol, silicone and oil, such as olive oil. The heat transfer fluid can comprise a deuterated molecule. Use of a deuterated molecule can avoid interference caused by Raman scattering due to the heat transfer fluid because the Raman spectra emitted by the deuterated molecule will be other than that of the light and the tissue. Preferably, the sheaths are sealed at the outer edges and around the window so that fluid cannot escape from between the inner and outer sheaths.

In one embodiment of the device, the window comprises a substantially annular opening or hole in the inner and outer sheaths. In another embodiment, the window comprises a lens. The window is preferably about 1 mm to about 10 mm in diameter. The lens can also be shaped so as to apply pressure to the tissue being probed, as a means of pressure modulation.

The inner and outer sheaths of the device can be substantially cylindrical in shape, comprise a fingerstall, and/or comprise a cuff. Preferably, the flexible material of the sheaths comprises latex In preferred embodiments, the device is of similar dimensions to a finger cot, also known as a fingerstall.

The flexible sheathing material allows for adaptation to various finger dimensions. Preferably, the overall length of the device is about 6 cm and the overall diameter at the open end is about 2 cm. The device can employ a plurality of sheathing materials.

Figure 2:
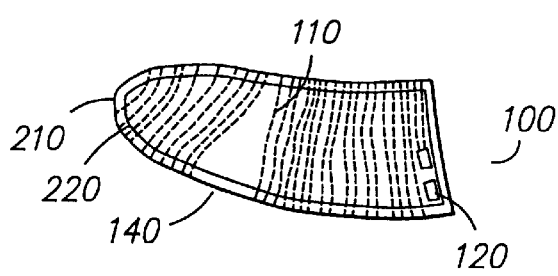
FIG. 2 is a side view of the tissue modulation device shown in FIG. 1.

In one embodiment, the inner and outer sheaths are separated by a gap of about 50 to about 1000 $\mu$m. An electrical connection to a thermocouple can be located near the open end of the apparatus. The gap between the two sheaths is preferably filled with approximately 1–2 ml of heat transfer fluid and the gap between the sheaths is sealed at the open end of the device where the finger is inserted as illustrated in FIGS. 1 and 2.

In another embodiment, the shape of the sheath is such that it fits snugly over the fingertip and up to the first finger joint. The inner and outer sheaths are connected around the wide end so that liquid does not leak out. In addition to the heating element, a thermoelectric cooler (such as a Peltier device) can be placed inside the two sheaths and separate electrical connections through the outer sheath can be made to the cooling element(s). Allowance is made for the electromagnetic radiation to contact the tissue through the window. Those skilled in the art can appreciate variations in the window that will permit bringing electromagnetic radiation into contact with the tissue for the purposes of taking measurements of emitted spectra.

In another embodiment, the device comprises means for altering the temperature of a region of tissue in a subject; means for securing the device to the tissue; and a window, wherein the window is sufficiently transparent that electromagnetic radiation can be delivered to and collected from an underlying tissue through the device. The means for altering the temperature of the region of tissue can comprise a heating element and/or a cooling element. The means for altering temperature can comprise a temperature regulating element as described hereinabove as well as any material capable of elevating or lowering the temperature of the tissue. In one embodiment, the means for securing the device to tissue comprises a sheath, a fingerstall, a cuff, a strap, a molded sample holder or an adhesive.

Various modifications of the device can be made to accommodate different embodiments of the method. For example, the device can be used with a pressure-inducing device resembling a small blood pressure cuff or fitted to an inflexible device, such as a fixed position sample holder. Pressure and/or thermal modulation can be used to effect tissue modulation.

Figure 3:
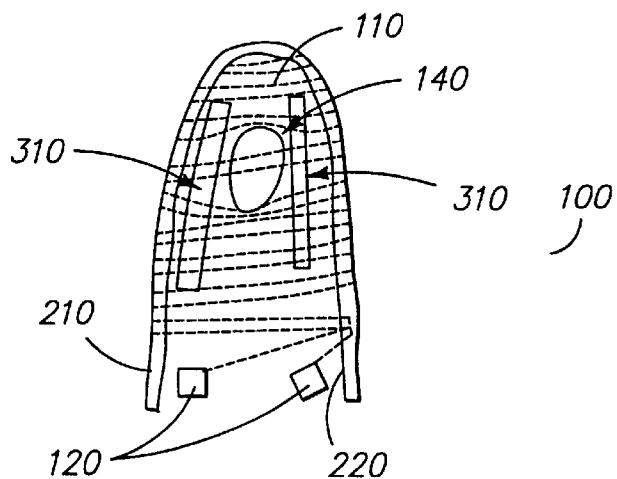
FIG. 3 is a bottom view of the tissue modulation device shown in FIG. 1.

A preferred embodiment of the device, which is designed to fit over a fingertip, is depicted in FIGS. 1–3. With reference to FIG. 1, a front view of the fingertip region shows the device 100, within which a heating wire 110 is coiled adjacent to the window 140 through which spectroscopic measurements can be taken. A first pair of electrical connections 120 are attached to the heating wire 110, and a second pair of electrical connections 130 are attached to a thermocouple.

FIG. 2 shows a side view of the same device 100 of FIG. 1. This view shows the heating wire 110 positioned to accommodate the window 140. Also shown are the electrical connection 120 and the outer sheath 210 and inner sheath 220. FIG. 3 shows a bottom view of the same device 100, in which the positioning of the cooling elements 310 can be seen along the sides of the window 140 and, in this embodiment, perpendicular to the coils of the heating wire 110. Also shown are the electrical connection 120 and the outer sheath 210 and inner sheath 220.

With respect to the particular embodiment for use with a fingertip that is illustrated in FIG. 3, the device can comprise a hole with sealed edges through which an optical device for electromagnetic radiation detection can be employed. Cooling elements are located on either side of the distal hole. Preferably, the cooling elements are about 3 to about 5 mm in length and are placed approximately 1–2 mm to either side of the hole. The cooling elements can be positioned all up and down the length of the finger as well.

In a preferred embodiment, the device is part of an apparatus or system that additionally includes means for irradiating the tissue with a light source and/or means for collecting and detecting light emitted by the irradiated tissue. One or more beamnsplitters and additional lenses, filters and collimators can be introduced into the light path to modify the light entering and/or exiting the tissue.

Figure 5:
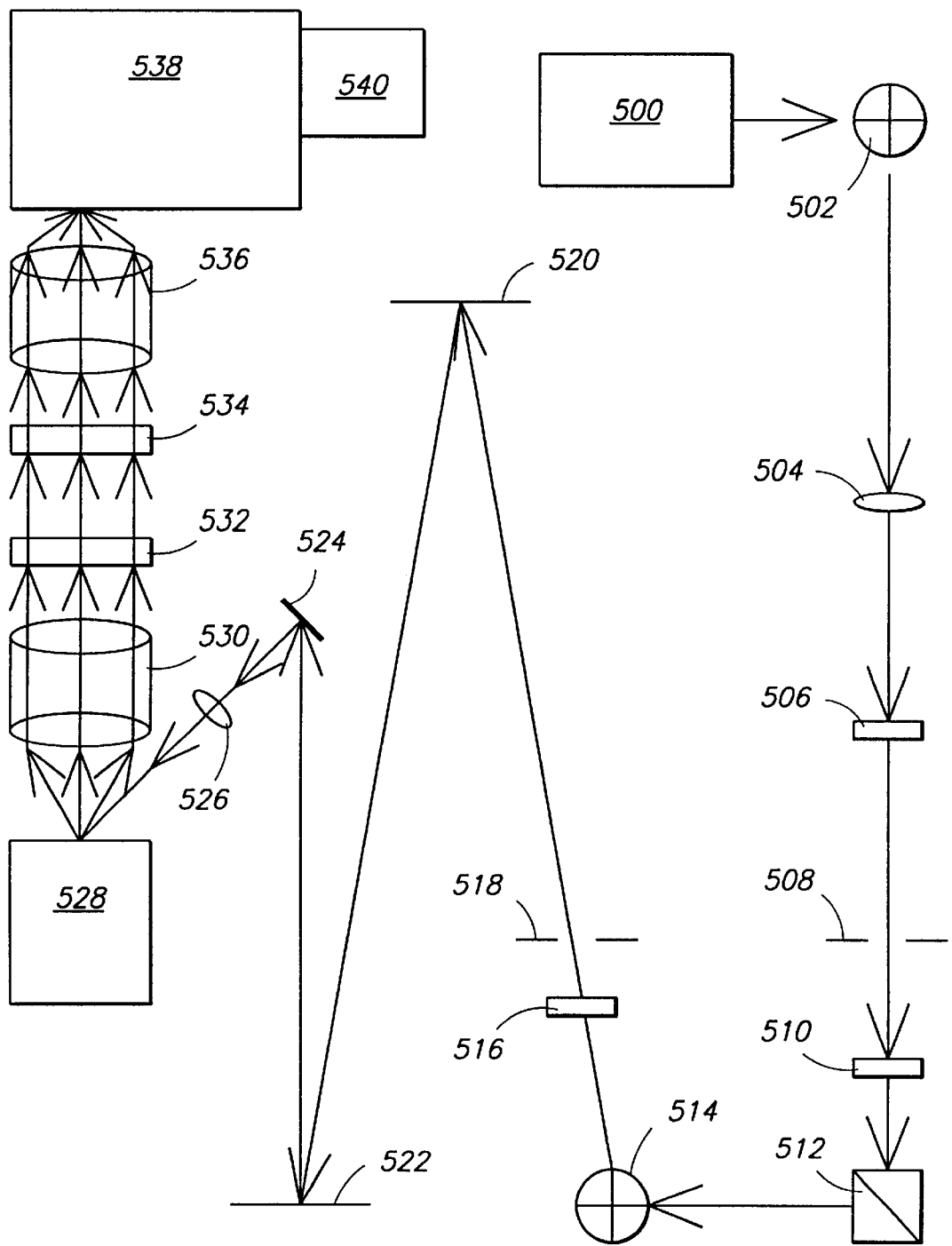
FIG. 5 is a schematic representation of a two-lens system for delivering light to and collecting light from a tissue for spectroscopic probing.

A schematic representation of a preferred system for spectroscopic probing of a tissue is depicted in FIG. 5. A source of electromagnetic radiation, such as a laser 500, directs light through a periscope 502. The periscope assists in alignment of the light with the entrance slit of the spectrograph 538. From the periscope 502, light then passes through a lens 504 having a long focal length, e.g., f=4.0 m, which corrects for divergence. The light then passes through a half-wave plate 506, which serves to rotate the polarization of the light to optimize function of the holographic bandpass filter. Next, light passes through an iris 508 and a metal/dielectric filter 510, both of which serve to remove light of undesirable wavelengths. Light then passes through a holographic bandpass filter 512, and a second periscope 514, which maintains alignment of the light with the entrance slit of the spectrograph 538. The polarization of the light is rotated again to achieve S-polarized light with respect to the entrance slit of the spectrograph 538 via a second half-wave plate 516. light passes through another iris 518, a series of three mirrors 520, 522, 524 and a focusing lens 526, which focuses the light onto tissue in the sample holder 528, where the tissue modulation device would be positioned.

Emitted light is then made parallel by a camera lens 530 before entering a polarizer 532, the latter removing polarization shifted light. Light then passes through a holographic notch filter 534 to remove light that is not shifted in wavelength, and then through another camera lens 536, focusing light onto the spectrograph 538, to which a detector 540 is coupled. The detector can be, for example, a multichannel or single channel detector. Examples of detectors include, but are not limited to, a CCD array, microbolometer array, an avalanche photodiode or a photomultiplier.

Methods of the Invention

The invention provides a method of measurement of blood volume simultaneously with measurements of a signal or signals indicative of blood analyte levels, conformation and states of aggregation. The blood volume measurement affords the necessary normalization of the blood analyte measurements to allow computation of concentration levels. The conformation and states of aggregation data can be related mathematically to lipid content and type and to protein content and type. Magnitude of measured changes as a function of temperature are approximately proportional to content.

Raman spectroscopy can be used to obtain information about fatty acids and phospholipids. The 2850 $cm^{-1}$ Raman band is the C-H symmetrical stretching mode, and is relatively constant in intensity under varying temperatures. The intensity ratio of 2890 and 2850 $cm^{-1}$ bands is used to monitor the transition temperature, that is melting temperature, of lipids and phospholipids (Brown, K. G. et aL, 1973, Biochem. Biophys. Res. Commun. 54:358; Larsson, K, 1973, Chem. Phys. Lipids 10:165; Mendelsohn, R., 1973, Nature 243:22). The ratio of 2890 $cm^{-1}$ band to 2850 $cm^{-1}$ band will shift as a function of temperature, decreasing as temperature rises. A plot of this ratio as a function of temperature will shift toward higher ratios at higher temperatures for saturated fats and plain lipids, while shifting in the opposite direction for unsaturated fats and phospholipids. Thus, the noninvasive methods of the invention can be used to obtain information about the identity and content of lipids in a subject.

Temperature and pressure can be used to affect the capillary content and, although these can be controlled to a large extent, it will be desirable to devise specific apparatus to aid in normalization. The present invention allows a normalization which is less vulnerable to error due to differences between individual anatomy and blood flow patterns. It also aids in the integration of the mechanical requirements for tissue modulation with the optical system needed to affect the blood/fluid/tissue analyte measurements.

The method comprises irradiating the tissue in a blood-replete state (warm or no pressure) with electromagnetic radiation having an excitation wavelength and collecting the spectra emitted by the tissue in the blood-replete state (warm, or no pressure). The method further comprises irradiating the tissue in a blood-depleted (cool, or pressured) state with electromagnetic radiation having an excitation wavelength and collecting the spectra emitted by the tissue in the blood-depleted (cool, or pressured) state. The method additionally comprises analyzing the collected spectra to determine a concentration of analyte present in the tissue, wherein the analyzing comprises determining the difference between the spectra collected in the blood-replete (warm) and blood-epleted (cool) states. Examples of spectra that can be collected include, but are not limited to, Raman, nuclear magnetic resonance (NMR), electron spin resonance (ESR), UV-visible absorption, infrared absorption, fluorescence and phosphorescence spectra.

In preferred embodiments, the tissue is blood, such as blood circulating in capillary beds of the fingertip. Other tissues can be used, such as ear lobe, muscle, skin, breast or brain. The subject is preferably a vertebrate, such as a mammal bird, reptile or fish. Examples of mammals include, but are not limited to, human, bovine, porcine, ovine, murine, equine, canine, and feline. In a most preferred embodiment, the subject is human.

Figure 4:
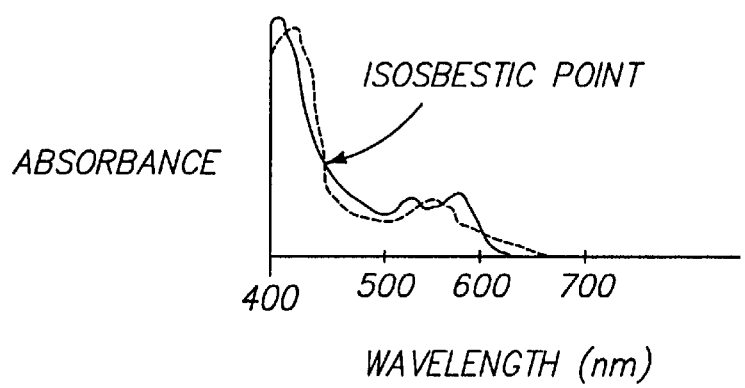
FIG. 4 is a graph illustrating the determination of an isosbestic point.

In preferred embodiments, the analyzing employs the determination of blood volume by contacting the tissue modulated region with light chosen to have a wavelength at an isosbestic point of, for example, the oxydeoxyhemoglobin binary equilibrium (805 and 580 nm), as demonstrated in FIG. 4. The amount of light which returns is approximately inversely related to the volume of blood in the contacted region.

In one embodiment, the invention provides a method of modulating temperature of tissue in a subject to be spectroscopically probed. In a preferred embodiment, the method comprises applying a tissue modulation device of the invention to the tissue, passing current through the temperature regulating element so as to elevate or lower the temperature of the tissue, and passing electromagnetic radiation through the window of the device. Preferably, spectroscopic probing is performed when the temperature of the tissue has been elevated or lowered and when the temperature of the tissue is not elevated or lowered. The method can further comprise collecting Raman spectra emitted by the tissue. The collected Raman spectra can then be analyzed, the analysis including a comparison of spectra emitted in the different temperature states.

The invention also provides a method for monitoring phase transitions and conformational changes, and thereby a method for determining lipid content and identity and protein content in a tissue of a subject. In a preferred embodiment, the method comprises applying a tissue modulation device of the invention to the tissue, passing current through the temperature regulating element so as to elevate or lower the temperature of the tissue, and passing electromagnetic radiation through the window of the device. Preferably, spectroscopic probing is performed when the temperature of the tissue has been elevated or lowered and when the temperature of the tissue is not elevated or lowered. The method can further comprise collecting Raman spectra emitted by the tissue. The collected spectra are then analyzed to determine the lipid content, lipid identity and/or protein identity, protein content of the tissue. Preferably, the analysis comprises determining the difference in number of Raman shifted photons emitted by the tissue at different temperatures.

EXAMPLES

The following examples are presented to illustrate the present invention and to assist one of ordinary skill in making and using the same. The examples are not intended in any way to otherwise limit the scope of the invention.

Example 1
Raman Shift Observed With Temperature Modulation

This example illustrates the order-disorder transition of lipids at least 6–30 microns beneath the surface of the skin using purely thermal modulation. The results show that noninvasive in vivo Raman spectroscopy can be used to obtain information about the identity and content of lipids.

Materials & Methods

A schematic diagram of the optical set up is shown in FIG. 5. A 785 nm, amplitude and wavelength stabilized, external cavity, CW laser 500, (SDL XC30, SDL Inc., San Jose, Calif.) produces a maximum total power of 300 mW. More than half of this power is associated with a large, spectrally wide and unsymmetrical base of amplified spontaneous emissions (ASE). This is adequate to obtain Raman spectra of simple, less challenging samples, i.e. virtually any in vitro sample. To obtain acceptable in vivo spectra, however, a substantial amount of the ASE should be removed. This is done using a holographic bandpass filter 512 (Kaiser Optical Systems, Ann Arbor, Mich.). While this does not remove all of the disturbing background radiation, it is adequate to allow in vivo spectra to be obtained.

Optics for correcting the spatial arrangement of the fast and slow axes of the laser divergence, as well as for obtaining the optimum polarization for diffraction efficiency and background reduction in the f1.4 holographic spectrograph 538 (Holospec, Kaiser Optical Systems, Ann Arbor, Mich.), eventually allow us to bring only about 50 mW of laser power to the sample. All optics are antireflection coated for 785 nm and a 13 cm focal length lens 526 is used to finally bring the light to the tissue in question. An angle of incidence of approximately 53' gives acceptable results. The light collection system uses two 50 mm f1.4 Nikon camera lenses 530, 536, a holographic notch filter 534 (Kaiser Optical Systems, Ann Arbor, Mich.) and a Polacor™ (Corning) polarizer 532 to bring the scattered light from the sample to the entrance of the spectrograph 538. The detection system 540 is an IR enhanced, liquid nitrogen cooled CCD array from Princeton Instruments. The resolution of the spectrograph system is 6 cm$^{-1}$ with wavenumber accuracy of 6 cm$^{-1}$ using a calibration based on known lines in atomic emission spectra.

The samples for all the experiments reported in this example were the fleshy side of the finger tips of human subjects, on the side opposite the finger nail Essendally identical results were obtained using any of the fingers and either hand. The sample holder 528 itself, which we have termed the tissue modulator (TM), is important to obtaining reproducible results for either of the two types of experiments presented in this example. The TM combines the electromechanical elements required to perform tissue modulation with a set of focussing optics to bring the excitation light to the sample so that precise optical alignment can be maintained throughout the procedure.

The TM used for this example contains an orifice, against which the finger tip is placed, so that the tissue to be interrogated is accessible to the 785 nm excitation light through the orifice. There is a spring loaded plunger arrangement which can be placed in a retracted position so that it does not place pressure against the back of the finger. Alternatively, the plunger can be released so that a padded, complementary shaped piston presses against the back and side surfaces of the finger, thereby aiding the volunteer in squeezing the finger tip against the orifice. Any difference in absolute position of the finger surface in either plunger position was found to be negligible and irrelevant.

When the finger is simply placed in the TM without any pressure between the finger and the orifice, the finger is in the unsqueezed state. In this state, the blood volume is normal and the flow patterns and net rate into and out of the region is normal. When the plunger is released, and the volunteer presses the finger against the orifice, the blood flow to the 785 nm exposed finger tip is restricted, and at equilibrium, the blood and fluid content, and possibly the chemical nature, e.g. oxygenation, of those fluids in the region inside the orifice is changed. The finger is then in the squeezed state.

To achieve good mechanical pressure modulation, the total pressure involved varies somewhat from sample to sample but never exceeds about 1 Newton. The TM has a built-in stop that the user can adjust to obtain optimal pressure with an acceptable comfort level for the squeezed state. When the plunger is retracted, the subject places his or her finger just touching against the orifice and holds it motionless while the spectrum is obtained Different sized and shaped orifices are optimal for different size fingers and different types of tissue modulation. For the present results, a round orifice 0.95 cm in diameter was used and the average finger was 5.3 cm in circumference.

Visual inspection shows that, regardless of the shapes, in the squeezed state there is always a pale blood depleted region, within a millimeter, just adjacent to where the orifice edge makes physical contact with the skin surface. A circularly shaped orifice, of appropriate size relative to the size of the finger tip, also produces in the squeezed state a circular area inside the blood depleted edge region which, still contains some blood. The amount of blood inside this region is not precisely known at this time but should be somewhat less because of the net applied pressure. For the present, it is clear that there is a gradient of blood volume between this inner region and the outer depleted region.

Visual inspection using an in-line video system with magnification shows that when the system is aligned initially in the unsqueezed state, the light impinges near the center of the orifice. In going to the squeezed state, i.e. the volunteer doing nothing more than pushing against the TM orifice, the point where the excitation laser contacts the finger tip moves slightly, impinging into the blood depleted region. The results show that moving and changing how the laser contacts the finger tip without increasing the pressure between the finger tip and the orifice results in no modulated spectrum. Therefore, in the squeezed state the laser interacts with a blood depleted region compared to the unsqueezed state.

Results

Among the test subjects used in this example are several Caucasian adults of varying heights and weights and an African American male and female. All of the subjects were in good health at the time of their participation and, with respect to the laser excitation, none experienced pain or discomfort of any kind during or after the testing. The results for the different individuals are all essentially identical. Experiments were performed utilizing mechanical pressure and temperature as tissue modulating stimuli.

Figure 6:
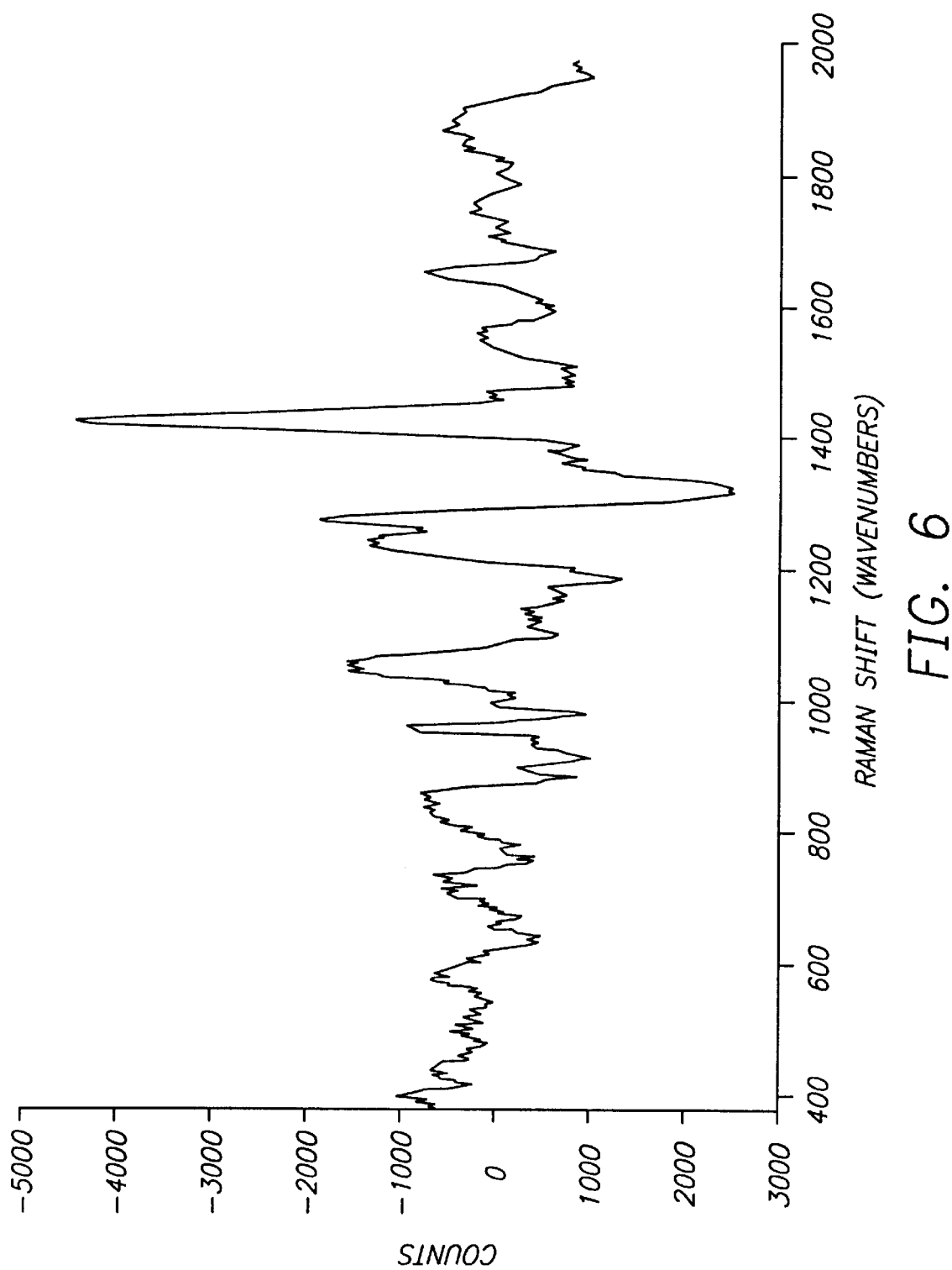
FIG. 6 is a graph showing the number of Raman shifted photons at wave numbers below 2000 $cm^{-1}$ after subtracting measurements taken from a cooled finger tip from measurements taken from the same finger tip at room temperature.

Representative results obtained from a single subject exposed to temperature modulation (no finger pressure applied) are shown in FIGS. 6–11. Raman spectra were collected over a period of 6 minutes from the subject's finger tip at room temperature, and for an additional 6 minute period after cooling. The finger tip was cooled by placing it in a glass of ice water for a few minutes until the subject could no longer tolerate the cold. FIG. 6 shows the number of Raman shifted photons (counts) at various wavenumbers after subtraction of measurements taken in the cold condition from those taken at room temperature. The peaks observed at approximately 1050 and just above 1400 correspond to peaks known from in vitro studies to occur as a result of a temperature shift. The peaks observed just above 1200 provide information about lipids, which congeal at cooler temperatures, and also proteins, which are denatured at higher temperatures.

An empirical baseline subtraction procedure was used in the analysis. Each raw spectrum was subjected to a 101 point adjacent averaging smoothing algorithm Each smoothed resultant was subtracted from the corresponding original raw spectrum and the difference subjected to a 7 point adjacent averaging smoothing algorithm. While the smoothed difference of the raw spectra was identical to the difference between the smoothed raw spectra, only the smoothed version of the difference was used in the analysis. Consideration of only the smoothed version of the difference between the raw spectra avoids introduction of differences between potential artifacts introduced by empirical baseline subtraction.

Other baseline subtraction procedures were employed, such as nonlinear least squares, to approximate the shape of the raw curves with a log nornal or binomial distribution and other functions. Using these functions to perform the same subtraction procedure obtained results consistent with those shown in FIG. 6. Application of the pure smoothing based procedure to a spectrum consisting of one narrow peak on a simulated background reveals a well-known tendency to introduce small negative dips on either side of the real peak The depth of these artifacts depends on the relative size of the broad background and the narrow feature. Given this predictable behavior as a caveat, the spectra disclosed herein can be compared with others in the literature. Another strategy is to perform the method using longer wavelength excitation, thereby inducing less broadband fluorescence.

Figure 7:
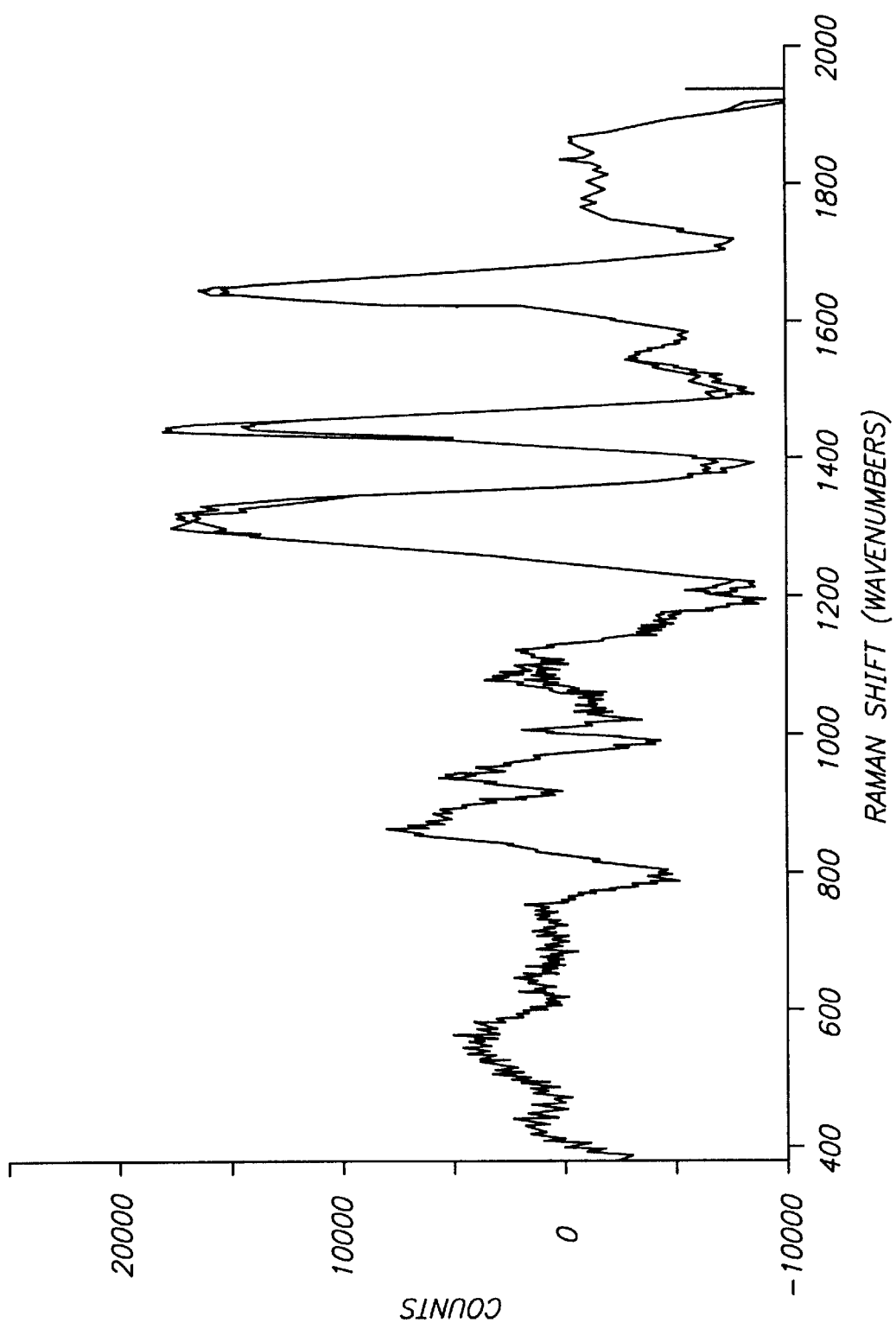
FIG. 7 is a graph showing the data of FIG. 6 in raw form (prior to subtraction). The upper trace (see peak near 1450 $cm^{-1}$) shows spectra collected from cooled tissue. The lower trace shows spectra collected at room temperature.
Figure 8:
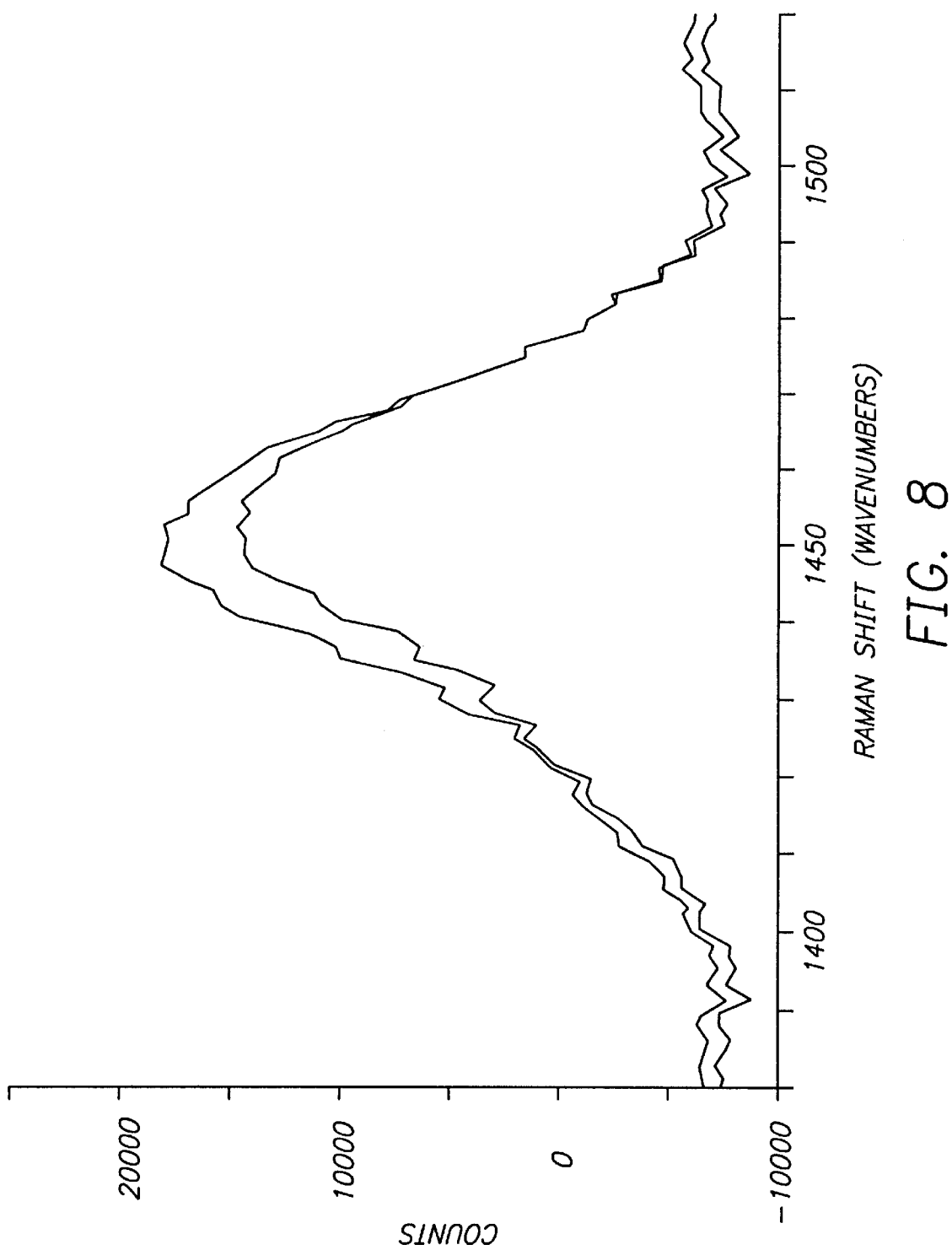
FIG. 8 is a graph showing the data of FIG. 7, but expanded to show the region of spectra near 1450 $cm^{-1}$.
Figure 9:
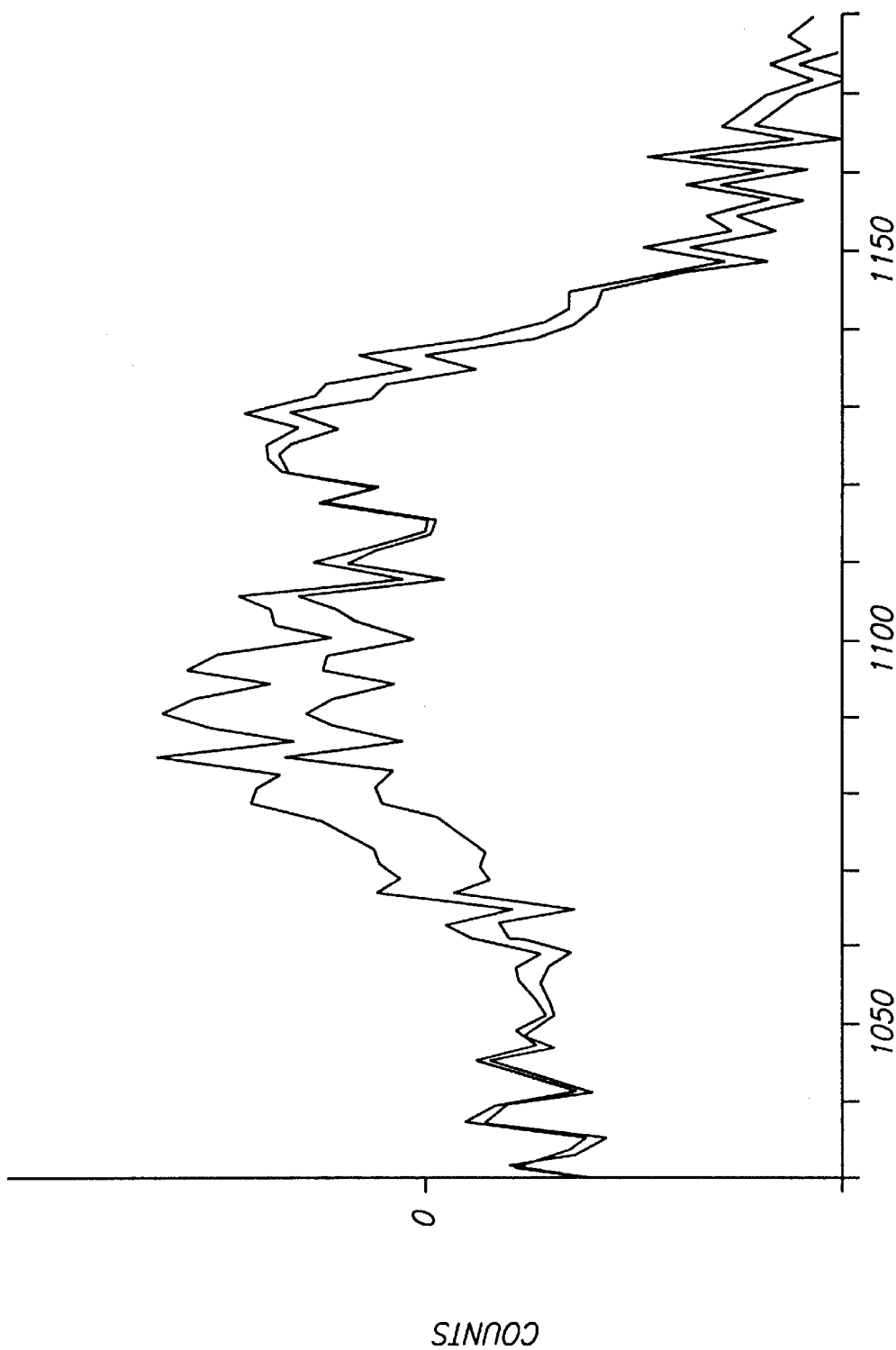
FIG. 9 is a graph showing the data of FIG. 7, but expanded to show the region of spectra near 1100 $cm^{-1}$.
Figure 10:
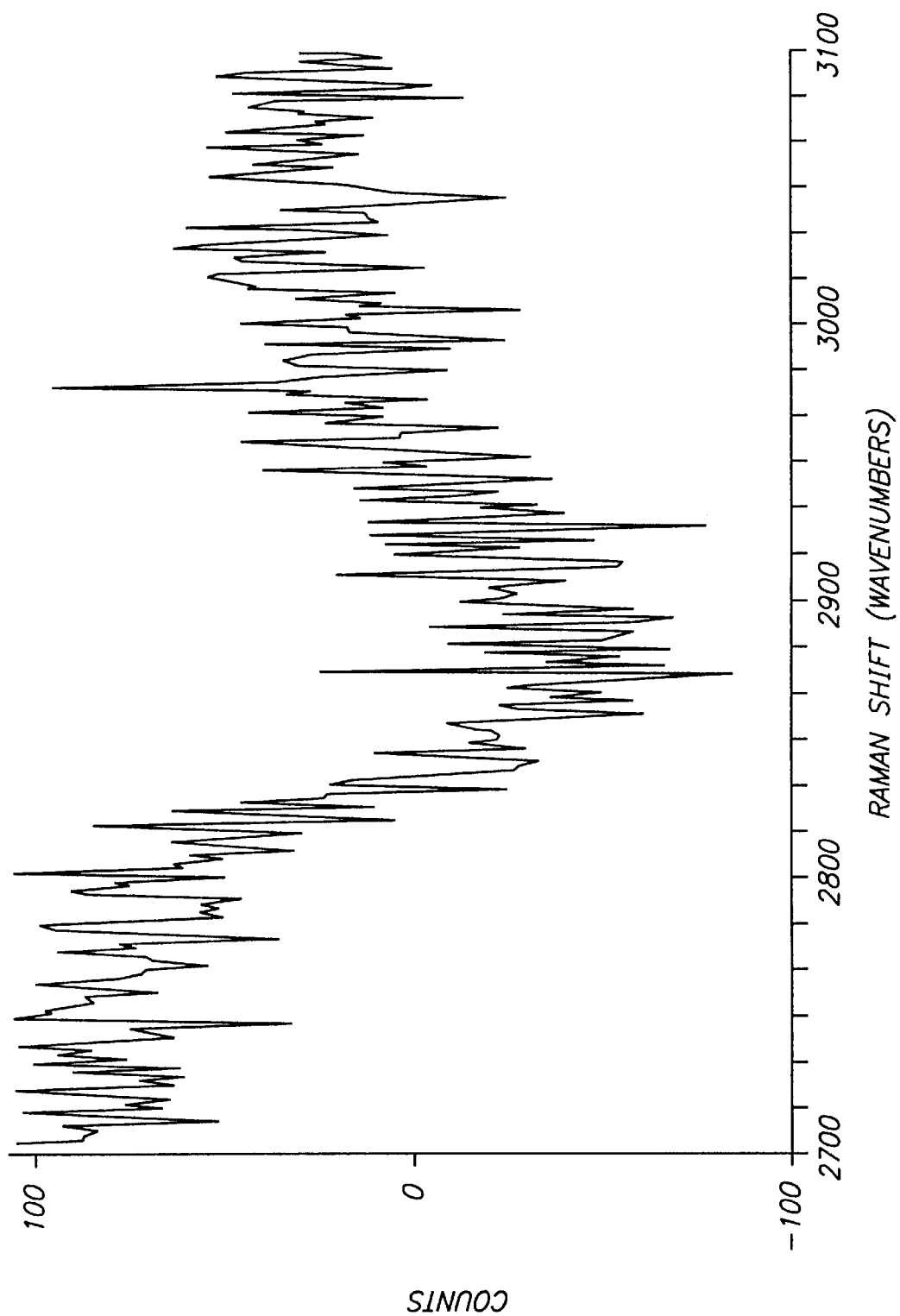
FIG. 10 is a graph showing the long shift data corresponding to the data shown in FIG. 6.
Figure 11:
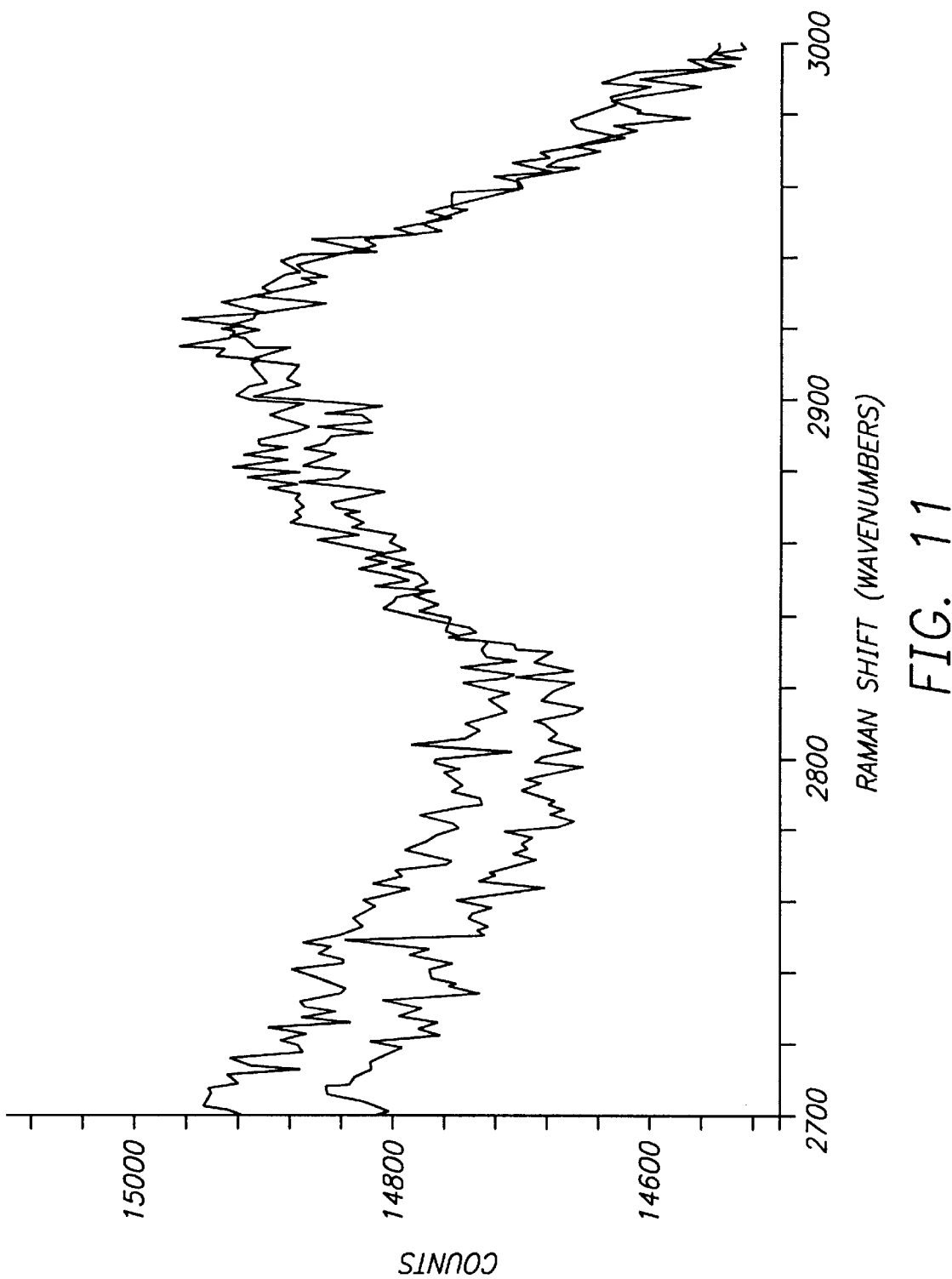
FIG. 11 is a graph showing the data of FIG. 10 in raw form (prior to subtraction). The trace that is lower at 2700–2800 $cm^{-1}$ and higher near 2900 $cm^{-1}$ shows data collected when the tissue was cooled, and the other trace shows data collected at room temperature.

FIG. 7 shows the same data as shown in FIG. 6, except in raw form, depicting separate traces for counts obtained at 0–2000 wavenumbers in the cold condition (upper trace) and at room temperature lower trace). In FIG. 8, the x-axis is expanded to show the difference between these two traces near 1450 wavenumbers. FIG. 9 shows the difference near 1100 wavenumbers. FIG. 10 shows data as depicted in FIG. 6, but at higher wavenumbers. Note the peak at approximately 2980. FIG. 11 shows the same data as in FIG. 10, except in raw form, depicting separate traces for counts obtained at higher wavenumbers. The trace that is the upper trace at wavenumbers near 2900 is from the cold condition. Note that these data were obtained in just 17 seconds, indicating the speed with which these noninvasive measurements can be completed.

Example 2

Depth Discrimination

This example describes a confocal, four-lens system that can be used to determine the depth of a signal emitted by tissue that is spectroscopically probed. Determination of the depth of a source of emitted light permits identification of the type of tissue, e.g., skin, blood, and of the type of lipid, e.g., lipid, phospholipid, sphingolipid.

Figure 12:
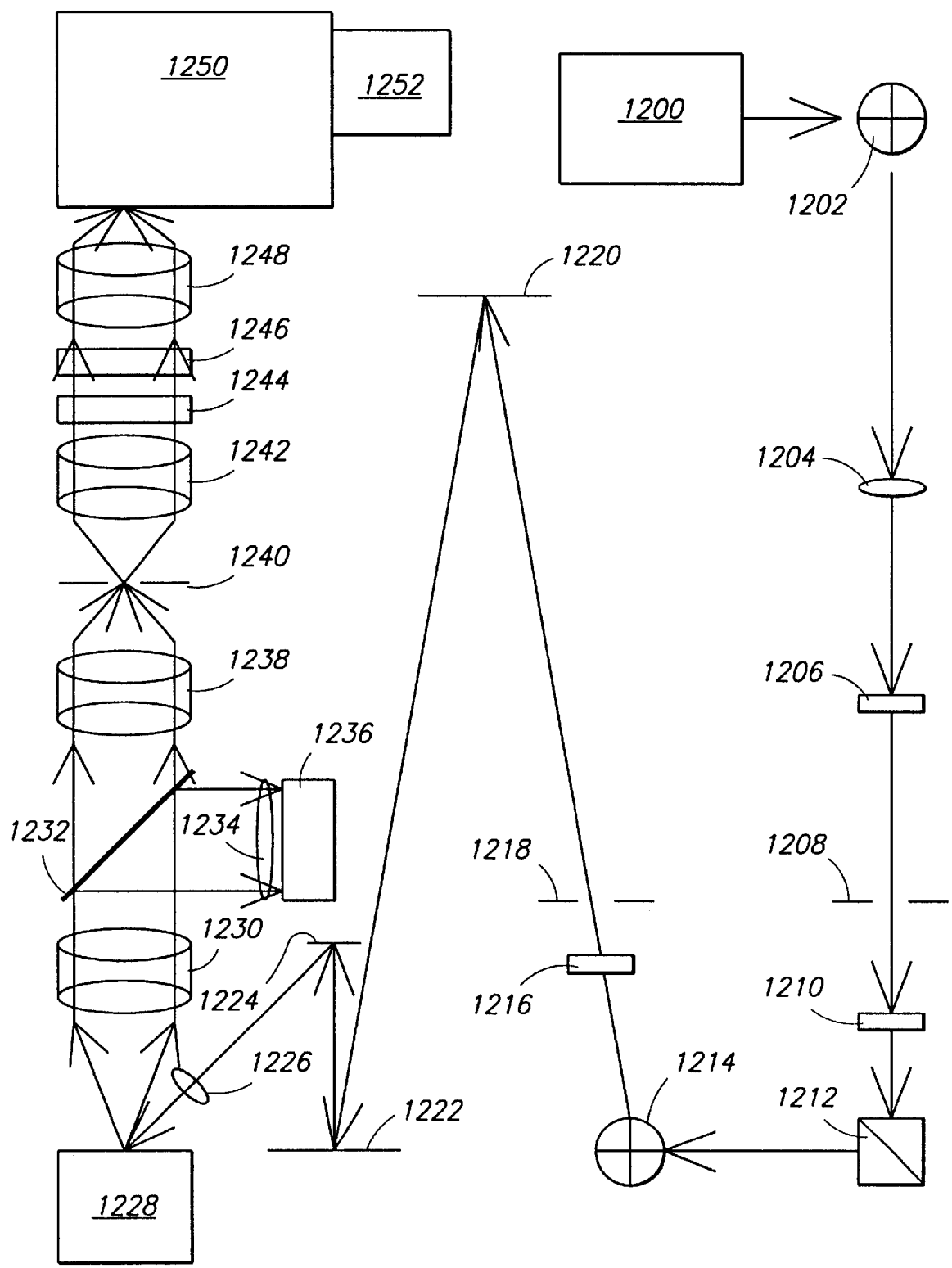
FIG. 12 is a schematic representation of a confocal, four-lens system for combining depth discrimination with spectroscopy.

A schematic representation of such a confocal, four-lens system is shown in FIG. 12. Light is directed from a laser source (SDL-XC30) 1200 to a periscope 1202, then through a 4 meter lens 1204, a half-wave plate 1206, in iris 1208, a metal/dielectric filter 1210, a holographic bandpass filter 1212, a second periscope 1214, a second half-wave plate 1216, a second iris 1218, a series of three mirrors 1220, 1222, 1224, and a focussing lens 1226, before ariving at the tissue, which is positioned in the sample holder 1228 (tissue modulation device). Light emitted by the tissue passes through a camera lens 1230 and on to a pellicle 1232, which directs some of the light to a CCD imaging camera 1236 after passing through a lens 1234. The remaining light from the tissue is directed through a second camera lens 1238, a confocal iris 1240, a third camera lens 1242, a polarizer 1244, a holographic notch filter 1246, and a fourth camera lens 1248, before the light enters the holographic spectrograph 1250 having a light collection efficiency of f=1.4, to which is coupled a CCD detector 1252.

Those skilled in the art will appreciate that the conceptions and specific embodiments disclosed in the foregoing description may be readily utilied as a basis for modifying or designing other embodiments for canying out the same purposes of the present invention. Those skilled in the art will also appreciate that such equivalent embodiments do not depart from the spirit and scope of the invention as set forth in the appended claims.

What is claimed is:

1. A tissue modulation device for use during noninvasive spectroscopy of tissue of a subject comprising an inner sheath, an outer sheath and a window disposed through the inner and outer sheaths, wherein the inner and outer sheaths comprise a sufficiently flexible material that the device can be secured to a region of tissue to be spectroscopically probed, wherein the inner and outer sheaths are joined to one another so that at least one temperature regulating element can be disposed between the inner and outer sheaths, and wherein the window comprises a substantially annular opening in the inner and outer sheaths such that electromagnetic radiation can be delivered to and collected from an underlying tissue through the annular opening in the inner and outer sheaths.

2. The device of claim 1, further comprising a temperature regulating element disposed between the inner and outer sheaths.

3. The device of claim 2, wherein the temperature regulating element comprises a heating element.

4. The device of claim 2, wherein the temperature regulating element comprises a cooling element.

5. A method of modulating temperature of tissue in a subject to be spectroscopically probed comprising:

(a) applying the device of claim 2 to the tissue;

(b) passing current through the temperature regulating element so as to elevate the temperature of the tissue; and (c) passing electromagnetic radiation through the window of the device.

6. The method of claim 5, wherein the tissue is a fingertip.

7. The method of claim 5, wherein step (c) is performed when the temperature of the tissue has been elevated and when the temperature of the tissue is not elevated.

8. The method of claim 5, further comprising collecting Raman spectra emitted by the tissue.

9. A method of modulating temperature of tissue in a subject to be spectroscopically probed comprising:
(a) applying the device of claim 2 to the tissue;
(b) passing cutrent through the temperature regulating element so as to lower the temperature of the tissue; and
(c) passing electromagnetic radiation through the window of the device.

10. The method of claim 9, wherein the tissue is a fingertip.

11. The method of claim 9, wherein step (c) is performed when the temperature of the tissue has been lowered and when the temperature of the tissue is not lowered.

12. The method of claim 9, further comprising collecting Raman spectra emitted by the tissue.

13. The device of claim 1, further comprising a temperature sensing element disposed between the inner and outer sheaths.

14. The device of claim 1, wherein the temperature regulating element comprises wire.

15. The device of claim 14, wherein the wire comprises teflon-coated nichrome.

16. The device of claim 1, further comprising a heat transfer fluid within the space between the inner and outer sheaths.

17. The device of claim 16, wherein the heat transfer fluid is selected from the group consisting of glycerol, silicone and oil.

18. The device of claim 16, wherein the heat transfer fluid comprises a deuterated molecule.

19. The device of claim 1, wherein the window further comprises a lens.

20. The device of claim 1, wherein the window is about 1 mm to about 10 mm in diameter.

21. The device of claim 1, wherein the inner and outer sheaths are substantially cylindrical in shape.

22. The device of claim 1, wherein the inner and outer sheaths comprise a fingerstall.

23. The device of claim 1, wherein the inner and outer sheaths comprise a cuff.

24. The device of claim 1, wherein the flexible material comprises latex.

25. A tissue modulation device for use during noninvasive spectroscopy of tissue of a subject comprising:
(a) a flexible material comprising a means for noninvasively altering the temperature of a region of tissue in a subject;
(b) means for securing the device to the tissue; and
(c) a window disposed through the flexible material, wherein the window is sufficiently transparent that electromagnetic radiation can be delivered to and collected from an underlying tissue through the device.

26. The device of claim 25, wherein the means for securing the device to tissue comprises a sheath, a fingerstall, a cuff, a strap, a molded sample holder or an adhesive.

* * * * *

UNITED STATES PATENT AND TRADEMARK OFFICE
CERTIFICATE OF CORRECTION

PATENT NO.    : 6,292,686 B1
DATED         : September 18, 2001
INVENTOR(S)   : Joseph Chaiken and Charles M. Peterson It is certified that error appears in the above-identified patent and that said Letters Patent is hereby corrected as shown below:

<u>Title page,</u>
Item [57], ABSTRACT,
Line 1, after "for use", "dining" should read -- during --.

Signed and Sealed this

Thirty-first Day of December, 2002

JAMES E. ROGAN
*Director of the United States Patent and Trademark Office*